(12) United States Patent
Zang et al.

(10) Patent No.: US 8,729,298 B2
(45) Date of Patent: May 20, 2014

(54) METHOD FOR SEPARATION AND PURIFICATION OF LONG-CHAIN DIACIDS

(75) Inventors: Huiqing Zang, Shanghai (CN); Guang Lei, Shandong (CN); Bingbing Qin, Shanghai (CN)

(73) Assignee: Cathay Industrial Biotech Ltd., Shanghai (CN)

( * ) Notice: Subject to any disclaimer, the term of this patent is extended or adjusted under 35 U.S.C. 154(b) by 115 days.

(21) Appl. No.: 13/371,803

(22) Filed: Feb. 13, 2012

(65) Prior Publication Data
US 2012/0253069 A1  Oct. 4, 2012

Related U.S. Application Data

(60) Provisional application No. 61/468,349, filed on Mar. 28, 2011.

(51) Int. Cl.
*C07C 51/42* (2006.01)
(52) U.S. Cl.
USPC .......................................................... 562/593
(58) Field of Classification Search
USPC ............ 560/206, 191, 190, 76, 78, 205, 218, 560/248; 562/400, 512, 590, 593; 554/185, 554/184, 1, 175
See application file for complete search history.

(56) References Cited

U.S. PATENT DOCUMENTS 6,218,574 B1 * 4/2001 Liu et al. ........................ 562/593

FOREIGN PATENT DOCUMENTS

CN 1219530 A 6/1999
CN 1255483 A 6/2000

OTHER PUBLICATIONS

Tedetti et al. (Determination of Low Molecular Weight Dicarboxylic and Ketocarboxylic Acids in Seawater Samples, Analytical Chemistry, 78, pp. 6012-6018, 2006).*
Klampfl et al. (Investigations on the Chromatographic Behavior of Carboxylic Acids on Silica-Based Cation Exchangers, J. Liq. Chrom. and Rel. Technol., 21(13), pp. 2069-2079, 1998).*
Jayaswal et al. (Effect of Chemical Modifications upon Exchange Capacity of Aminated Macroporous Styrene-Divinyl Benzen (PS-DVB) Copolymer Anion Exchange Resin, Journal of Applied Polymer Sciences,vol. 79, 1735-1748, 2001).*
The Free Dictionary (Downloaded from the Internet Jun. 25, 2013).*
Baogui Zhang, et al., The Investigation of Purifying Sebacic Acid With D-412 Chelating Resin, *Ion Exchange and Adsorption*, 1999, 15(3): 268-271.
Zhengfu Kou, et al., The Decolorization of Long Chain Dibasic Acid Broth by Using Adsorption Resin, *Ion Exchange and Adsorption*, 2003, 19(2): 180-184.

* cited by examiner

*Primary Examiner* — Wu-Cheng Winston Shen
*Assistant Examiner* — Blaine G Doletski
(74) *Attorney, Agent, or Firm* — Finnegan, Henderson, Farabow, Garrett & Dunner, LLP

(57) ABSTRACT

A method for the separation and purification of at least one long-chain diacid, comprising:
   introducing an impure preparation comprising at least one long-chain diacid to a stationary phase of a chromatograph; and
   eluting the at least one long-chain diacid from the stationary phase with at least one eluent.

19 Claims, No Drawings

METHOD FOR SEPARATION AND PURIFICATION OF LONG-CHAIN DIACIDS

This application claims benefit under 35 U.S.C. §119(e) of U.S. Provisional Application No. 61/468,349, filed Mar. 28, 2011, the contents of which are incorporated herein by reference.

Disclosed herein is a method for separation and purification of at least one long-chain diacid. Specifically, disclosed herein is a method for separation and purification of at least one long-chain diacid by means of chromatography.

Dicarboxylic acids comprising eight or more carbon atoms are commonly referred to as "long-chain diacids." Long-chain diacids can be used as basic constituent monomer for a series of synthetic materials. Potential uses of long-chain diacids and their derivatives include, for example, production of special nylon resins, polycarbonate, powder coatings, fragrances, hot-melt adhesives and special lubricants. Long-chain diacids can also be used as plasticizers for engineering plastics and corrosion inhibitors in, for example, metal processing technology. When used as constituent monomers for production of special nylon, long-chain diacids can demonstrate some unique performance characteristics when compared to other monomers.

Commercial quantities of long-chain diacids are generally not found in nature. Certain long-chain diacids, such as sebacic acid and dodecanedioic acid, can be prepared via chemical methods. For example, starting with benzene or 1,3-butadiene, dodecanedioic acid can be prepared through multiple steps of chemical reactions. Sebacic acid can be prepared through the chemical conversion of castor oil. Long-chain diacids can also be prepared via a biological method. A biological method, such as fermentation, can produce a series of long-chain diacids containing 9 through 18 carbon atoms. A major challenge to commercial production of long-chain diacid(s) via a biological method lies in separating and purifying the long-chain diacid(s) in a simple and low-cost way because of the similar structures between impurity acids and the target products. When alkane is used as substrate to produce long-chain diacids via fermentation, for example, a mixture of diacids with different chain length and monocarboxylic acids may be produced due to the alkanes having different chain length as the fermentation raw material and/or due to different metabolic pathways in the microorganism used to perform the fermentation. Also, for example, when fatty acid and/or its derivatives are used as the fermentation raw material, small quantities of fatty acid and its derivatives may remain in the fermentation product broth. Commercial applications of long-chain diacids may require them to be of very high purity with low quantities of color-inducing impurities and high heat stability. For example, as the basic constituent monomer for high-end nylons (such as Nylon 6,12 and Nylon 12,12), polymer-grade dodecanedioic acid may need to have very low monocarboxylic acid content, because monocarboxylic acid, can terminate the polymerization. The content of color-inducing impurities that may react under high temperature may also need to be very low because it may affect the color and performance of nylon. As another example, to comprise an ingredient in the fragrance Musk-T, tridecanedioic acid must have low impurity levels, because impurities, including different acids, can affect the fragrance of Musk-T.

The present inventors have surprisingly discovered that using chromatography for industrial separation and/or purification of long-chain diacids can achieve unexpected results. The target long-chain diacid(s) and impurities have different interacting forces with the chromatograph stationary phase. Under specific eluting conditions and/or with a specific chromatograph stationary phase, the differences between the interacting forces could be large enough to achieve separation and/or purification of different components.

Described below is a method for the separation and purification of at least one long-chain diacid by means of chromatography. The method, for example, can be suitable for industrial use.

As disclosed herein, "suitable for industrial use" means that the separation and purification method described herein is suitable for separating and/or purifying long-chain diacid at a commercial production scale (from 100 to over thousands of metric tons of long-chain diacids per year), at relatively low cost, and can be used practically for industrial production.

As disclosed herein, "impure preparation" means a preparation comprising at least one target compound and impurities that is to be subject to chromatography for separation and purification of the at least one target compound.

As disclosed herein, "pretreatment" means to remove the insoluble substances and other impurities such as mycelium from the fermentation broth through, for example, at least one means chosen from centrifugation, filtration, and pH adjustment. For example, pretreatment may be chosen from plate-and-frame filtration and membrane filtration after the fermentation broth is basified. In another embodiment, pretreatment uses membrane filtration.

As disclosed herein, "separation and purification of at least one long-chain diacid" means to obtain at least one long-chain diacid individually with the desired purity.

As disclosed herein, "stationary phase" refers to a chromatographic phase that is immobilized on a support. For example, the stationary phase can comprise at least one material chosen from adsorption resin, activated carbon, floridin, diatomite and silica gel.

In one embodiment, disclosed herein is a method for separation and purification of at least one long-chain diacid comprising:
   introducing an impure preparation comprising at least one long-chain diacid to a stationary phase of a chromatograph; and
   eluting the at least one long-chain diacid from the stationary phase with at least one eluent.

In some embodiments, the stationary phase of the chromatography is in the form of at least one column.

In some embodiments, the stationary phase comprises at least one material chosen from adsorption resin, activated carbon, floridin, diatomite and silica gel.

In some embodiments, the adsorption resin is chosen from macroporous adsorption resins. In some embodiments, the macroporous adsorption resin is chosen from nonpolar macroporous adsorption resins. In some embodiments, the macroporous adsorption resin is chosen from polar macroporous adsorption resins. In some embodiments, the stationary phase comprises adsorption resin and at least one material chosen from activated carbon, floridin, diatomite and silica gel.

In some embodiments, the stationary phase comprises activated carbon. In some embodiments, the stationary phase comprises both activated carbon and floridin.

In some embodiments, the stationary phase is in the form of a single column. In some embodiments, the stationary phase is in the form of multiple columns. When multiple columns are used, the stationary phase in each column can be the same or different.

In some embodiments, the eluent comprises at least one solvent chosen from water and organic solvents, such as methanol and ethanol. In some embodiments, the mobile phase comprises water. If the pH value of the feeding material is greater than 7, in some embodiments, the mobile phase may be water solution of methanol or ethanol. The mobile phase can also, for example, be water solution of at least one metal salt chosen, for example, from NaCl, KCl, and $CH_3COONa$. If the pH value of the feeding material is less than 7, the mobile phase can be chosen, for example, from organic solvents, such as methanol and ethanol.

In some embodiments, the impure preparation comprising at least one long-chain diacid is obtained via at least one biological method. In some embodiments, the impure preparation comprising at least one long-chain diacid is obtained via at least one chemical method.

In some embodiments, the at least one biological method is at least one fermentation process. In some embodiments, the impure preparation comprising at least one long-chain diacid is obtained from the fermentation broth produced via at least one fermentation process using at least one substrate chosen from $C_9$-$C_{18}$ alkanes, fatty acids and derivatives thereof. In some embodiments, the fermentation broth comprises at least one diacid chosen from $C_9$-$C_{18}$ diacids. In some embodiments, the impure preparation is the fermentation broth after being subject to pretreatment.

In some embodiments, the impure preparation comprising at least one long-chain diacid obtained from the mother liquor produced after recrystalization in at least one chemical process, or from waste liquor produced in at least one process chosen from biological and chemical production processes.

In some embodiments, the at least one long-chain diacid can be an $\alpha$, $\omega$-aliphatic diacid with the main chain comprising 8 or more carbon atoms, for example, alkane diacids and olefin diacids comprising from 9 to 18 carbons. For example, it can be $C_{10}$ diacid (sebacic acid), $C_{11}$ diacid (undecanedioic acid), $C_{12}$ diacid (dodecanedioic acid), $C_{13}$ diacid (tridecanedioic acid), $C_{14}$ diacid (tetradecanedioic acid), $C_{15}$ diacid (pentadecanedioic acid), $C_{16}$ diacid (hexadecanedioic acid), $C_{17}$ diacid, (heptadecanedioic acid) $C_{18}$ diacid (octadecanedioic acid), or $C_{18}$-9-olefin diacid. In some embodiments, the at least one long-chain diacid can be one single long-chain diacid, or a mixture of different long-chain diacids.

In some embodiments, the activated carbon is in particulate form.

In some embodiments, the stationary phase comprises at least one material chosen from diatomite and floridin. In some embodiments, the stationary phase comprises diatomite and at least one material chosen from activated carbon and adsorption resin. In some embodiments, the stationary phase comprises floridin and at least one material chosen from activated carbon and adsorption resin. In some embodiments, the pH value of eluent can be adjusted appropriately to prevent precipitation of the at least one long-chain diacid in the stationary phase.

When macroporous adsorption resin is used as the stationary phase, the pH value of eluent may need to be adjusted so that the at least one long-chain diacid does not precipitate, for example, the pH of the mobile phase can be adjusted to be slightly basic.

In addition, when macroporous adsorption resin is used as the stationary phase, the pH value of the impure preparation may need to be adjusted to be, for example, basic so that the at least one long-chain diacid does not precipitate.

In some embodiments, the at least one long-chain diacid can be in the acid form or salt form thereof.

The method described herein can be applicable to many processes, such as purification of diacid in chemical production process, and extraction and purification of diacid from fermentation broth obtained from a fermentation process using alkane or fatty acid and/or their derivatives as substrates. Moreover, the method described herein may also be applicable to recovering and separating long-chain diacids from mother liquor after crystallization or from biological or chemical waste liquor containing long-chain diacids.

In some embodiments, the biological fermentation refers to the biotransformation to generate the corresponding at least one long-chain diacid by using, for example, *Candida Tropicalis* with $C_{8-18}$ alkane hydrocarbon or fatty acid and/or their derivatives (for example, fatty acid ester) as substrates. Besides the corresponding at least one long-chain diacid, mycelium and water, the fermentation broth may also contain small amounts of at least one residual material, for example, chosen from alkane, carboxylic acid, hydroxyl carboxylic acid, dicarboxylic acid, and inorganic ions. In some embodiments, the at least one long-chain diacid is present in an amount ranging from about 0.1 to 25% by weight relative to the total weight of the fermentation broth.

In some embodiments, the impure preparation comprising at least one long-chain diacid comprises a mixture of two or more long-chain diacids with different carbon chain lengths. In some embodiments, after separation and purification, two or more long-chain diacids with different carbon chain lengths are separated and individually obtained with the desired purity.

The following examples serve to illustrate the disclosure without limiting the scope thereof.

EXAMPLE 1

A mixture of 3 g of sebacic acid (produced with chemical method, chemical purity (CP) of 98.5%, Sinopharm Chemical Reagent Co., Ltd.) and 3 g of tridecanedioic acid (Shandong Cathay Biomaterial Co., Ltd., DC13P, purity 97%) was placed in a beaker. A diluted alkali solution was added to the beaker. The resulting mixture was heated and turned into a 60 ml of transparent aqueous solution with pH of 8.5. The concentrations of sebacic acid and tridecanedioic acid were both each 5% by weight relative to the weight of the aqueous solution. At a speed of 2 BV/h, the solution was added into a 3 cm-diameter 60 cm-height separation column, which was filled with 350 ml of nonpolar macroporous adsorption resin (DOW, XAD418) as the stationary phase. Under the operating temperature of 30° C., the stationary phase was eluted with water (the pH of the water was adjusted to 9.0 with NaOH) at a flow rate of 2 BV/h. The eluent was collected, and the analytic results were as follows, the concentration of each diacid was determined by gas chromatography.

| Eluent | Concentration of sebacic acid (by weight) | Concentration of tridecanedioic acid (by weight) |
|---|---|---|
| 0-1.0 BV | 0.28% | 0.05% |
| 1.0-2 BV | 0.01% | 0.22% |

EXAMPLE 2

A fermentation broth containing dodecanedioic acid (DC12) was obtained by fermenting *Candida tropicalis* strain (CCTCC M203052) with n-dodecane as substrate.

An appropriate amount of NaOH was added into the fermentation broth to adjust its pH to 10.0. The broth was heated to 70° C. The so-treated fermentation broth was placed into a filtration circulation tank of a ceramic micro-filtration membrane system with 0.1 μm micro-filtration membrane. A clear fermentation broth was obtained via membrane filtration by using a material pump and keeping the in-membrane pressure at 0.15 MPa and the out-membrane pressure at 0.10 MPa.

16 L of macroporous adsorption resin (Dow, XAD418) was loaded evenly into 20 pieces of 3.3 cm-diameter polypropylene chromatography columns. Those columns were connected together with an automatic control system and a feeding pump to form a continuous chromatography system.

The DC12-containing fermentation broth prepared as set forth above was passed through the 0.1 μm ceramic micro-filtration membrane to remove the fermentation microbe cell mass and residual n-dodecane. A clear membrane solution (pH 8.5) was obtained. Tested by gas chromatography, the concentration of dodecanedioic acid was 6.2% by weight relative to the clear membrane solution. The light absorption value of the clear membrane solution at 260 nm was 13.2.

The clear membrane solution prepared as set forth above was passed through the continuous chromatography system, in which the operating conditions of continuous chromatography were as follows: temperature 30° C., system pressure 7 bar, feeding rate 1.2 L/h, and water (de-ionized water, pH value of the water was adjusted to 9.0 with NaOH) elution rate 5.7 L/h. Equilibrium of the continuous chromatography system was achieved in 24 h after the feeding.

The conditions of the eluted material were as follows:

Product collecting port: The concentration of dodecanedioic acid was 1.9% by weight relative to the collected product portion. The light absorption value at 260 nm was 0.81. Waste liquor port: The concentration of dodecanedioic acid was 0.2% by weight relative to the discharged waste liquor portion. The light absorption value at 260 nm was 3.5.

Thus, in accordance with the separation and purification method disclosed herein, at least one long-chain diacid can be separated simply and effectively out of the impurities such as color-inducing impurities, and different long-chain diacids existing in the impure preparation can also be separated in same way. In addition, the chromatographic separation and purification method disclosed herein may consume less acid and alkali, and generate less waste water and thus less pollution, which can be an important industrial goal to achieve.

What is claimed is:

1. A method for separation and/or purification of at least one diacid comprising 8 or more carbon atoms comprising:
   introducing an impure preparation comprising at least one diacid comprising 8 or more carbon atoms to a stationary phase of a chromatograph; and
   eluting the at least one diacid comprising 8 or more carbon atoms from the stationary phase with at least one eluent,
   wherein the at least one diacid comprising 8 or more carbon atoms is present in a basic condition when introduced to the stationary phase and when eluted with the at least one eluent.

2. The method according to claim 1, wherein the stationary phase of the chromatography is in the form of at least one column.

3. The method according to claim 2, wherein the stationary phase of the chromatography comprises at least one material chosen from adsorption resin, activated carbon, floridin, diatomite and silica gel.

4. The method according to claim 3, wherein the adsorption resin is chosen from macroporous adsorption resins.

5. The method according to claim 4, wherein the macroporous adsorption resin is chosen from nonpolar macroporous adsorption resins.

6. The method according to claim 3, wherein the stationary phase of the chromatography comprises at least one adsorption resin and at least one material chosen from activated carbon, floridin, diatomite and silica gel.

7. The method according to claim 2, wherein the stationary phase of the chromatography is in the form of a single column.

8. The method according to claim 2, wherein the stationary phase of the chromatography is in the form of multiple columns.

9. The method according to claim 1, wherein the eluent comprises at least one solvent chosen from water and organic solvents.

10. The method according to claim 9, wherein the eluent comprises water.

11. The method according to claim 1, wherein the impure preparation is obtained via at least one biological method.

12. The method according to claim 11, wherein the at least one biological method is at least one fermentation process.

13. The method according to claim 12, wherein the impure preparation is obtained from fermentation broth obtained via the at least one fermentation process.

14. The method according to claim 13, wherein the fermentation broth comprises at least one diacid chosen from C9-C18 long-chain diacids.

15. The method according to claim 12, wherein the impure preparation is the fermentation broth after being subject to pretreatment.

16. The method according to claim 11, wherein the impure preparation is obtained from the waste liquor obtained via at least one biological method.

17. The method according to claim 1, wherein the impure preparation is obtained via at least one chemical method.

18. The method according to claim 17, wherein the impure preparation is obtained from the mother liquor after recrystallization and/or waste liquor produced in the at least one chemical method.

19. The method according to claim 1, wherein the impure preparation comprises a mixture of two or more diacid comprising 8 or more carbon atoms with different carbon chain lengths.

* * * * *